US006592866B2

(12) United States Patent
Walther et al.

(10) Patent No.: US 6,592,866 B2
(45) Date of Patent: Jul. 15, 2003

(54) NON-SELFDEGRADING ENDOPROTEASE

(75) Inventors: Bernt Th. Walther, Bergen (NO); Chunjun J. Rong, Bergen (NO)

(73) Assignee: Aqua Bio Technology AS, Eikelandsosen (NO)

( * ) Notice: Subject to any disclaimer, the term of this patent is extended or adjusted under 35 U.S.C. 154(b) by 0 days.

(21) Appl. No.: 09/988,588

(22) Filed: Nov. 20, 2001

(65) Prior Publication Data

US 2002/0064857 A1 May 30, 2002

Related U.S. Application Data

(63) Continuation-in-part of application No. 09/581,026, filed as application No. PCT/NO98/00378 on Dec. 11, 1998, now Pat. No. 6,346,245.

(30) Foreign Application Priority Data

Dec. 11, 1997 (NO) ............................................. 975826

(51) Int. Cl.[7] ........................... A61K 38/48; C12N 9/64

(52) U.S. Cl. ................ 424/94.1; 424/94.64; 424/94.63; 435/219; 435/226; 530/350; 530/412; 530/413; 530/416; 530/417

(58) Field of Search ........................... 424/94.63, 94.64, 424/94.1; 435/219, 226; 530/412, 413, 416, 417

(56) References Cited

FOREIGN PATENT DOCUMENTS

EP 0292663 11/1988

OTHER PUBLICATIONS

Choko Kawabata et al., "Miltpain, New Cysteine Proteinase From the Milt of Chum Salmon," *Comp. Biochem. Physiol.*, vol. 117B, No. 3, 1997, pp. 445–452.

F. Lahnsteiner et al., "Composition of the Ovarian Fluid in 4 Salmonid Species: Oncorhynchus Mykiss, Salmo Trutta f Lacustris, Salvelinus Alpinus and Hucho Hucho," *Reprod Nutr Dev*, vol. 35, 1995 pp. 465–474.

Z. Luberda et al., "Catalytic Properties of Hatching Enzyme of Several Salmonid Species," *Arch. Hydrobiol.*, vol. 131, No. 4, Oct. 1994, pp. 503–511.

C.J. Rong et al., "Endorproteolytic Hatching Enzyme From Atlantic Salmon (Salmo Salar) Embryos," University, Tromsoe, Norway, p. 127, 1994, *Dialog Information Services, File 44, Aquatic Sci & Fish Abs* No. 3627748.

Kunert, Mycoses (1992) 35(11–22):343–348.

Harris and Angal, "Protein Purification Methods: A Pratical Approach," N.Y., Oxford University Press, 1989, pp. 57–64, 151–161.

*Primary Examiner*—Christopher S. F. Low
*Assistant Examiner*—Chih-Min Kam
(74) *Attorney, Agent, or Firm*—Young & Thompson

(57) ABSTRACT

The present invention relates to a novel endoproteolytic hatching enzyme called zonase. The new enzyme is a non-selfdegrading endoprotease.

The inventors have purified the enzyme to sequence grade, this was made possible due to the described purification method, which set forth the sequence in which the purification method is to be performed. All preparations of salmon zonases exhibit valuable enzymatic properties with regard to proteolysis, both in terms of catalysis and stability.

7 Claims, No Drawings

NON-SELFDEGRADING ENDOPROTEASE

CROSS-REFERENCE TO RELATED APPLICATIONS

This application is a continuation-in-part of application Ser. No. 09/581,026 filed on Jun. 8, 2000 now U.S. Pat. No. 6,346,245, which is a 371 of PCT/NO98/00378 filed on Dec. 11, 1998.

The present invention relates to an etidoproteolytic hatching enzyme denoted zonase. This novel enzyme is a non-selfdegrading endoprotease. A procedure for extracting said enzyme in waste water from hatcheries producing Atlantic salmon larvae, and a simple procedure for obtaining up to sequence-grade purity of this special endoprotease, which turns out to possess rather unique proteolytic characteristics is described.

Proteases in purified states are increasingly used in research, in laboratory and clinical analysis, and in food production procedures. Demand is increasing, especially for enzymes with properties commensurate with specific applications. This has stimulated quests for new sources of proteases, which allow safe, sustainable and economical modes of production.

Here we exploit a new, rich source of endoproteases connected to aquaculture of Atlantic salmon. An essential aspect of this industry is the hatchery-production of developing eggs, which hatch to yield larva. Hatching is accomplished by embryos producing endoproteases, which, when secreted, effectively and specifically split the eggshell open to allow the larva to swim out and start life on its own (Refs.: Yamagami 1988; Walther 1993).

The crucial enzymes causing fish hatching have only been characterized in a few fishes, and in almost all cases, these hatching enzymes have been interpreted to be metalloproteases (Refs.: Hagenmaier 1974: Ohzu & Kasuya 1979; Schoots & Denucè 1981; DiMichele et al. 1981; Yasumasu et al. 1989 a, b. Araki & Onozato 1990; Hung et al. 1997). Genetic structure of some hatching enzymes has only recently become available (Ref.: Yasumasu et al. 1992).

Putative hatching enzymes have also been reported in invertebrates, where again most such enzymes have been interpreted as being metalloproteases (e.g. Barrett & Edward 1976; Lepage & Gache 1989; Roe & Lennarz 1990). However, a few strong cases for serine protease-like zonases have been reported (e.g. Post et al 1988). Conversely, among higher vertebrates than fish, putative hatching enzymes have also been reported.

For instance, both Urch & Hedrick (1981; concerning amphibians) and Yamazaki et al (1994; concerning mouse) reported zonases, which appeared to be serine proteases. The biological and biochemical rationale behind two different types of hatching enzymes among hatching animals is at present not fully understood.

Non-selfdegrading endoproteases are unique. In nature the destructive effects of proteases on biological tissues mandate that it is a functional adaption that proteases should self-destruct. For instance, this is the case for pancreatic endoproteases which otherwise might damage and ulcerate the intestine with serious injury to the individual. The situation is dramatically different during the hatching process for fish. If the crucial enzymes allowing hatching by degrading the eggshell (chorion, zona, or vitteline envelope) were to attack each other by proteolysis, the eggshell may survive intact and the individual would not be born, but die intra ovo. Hence the enzyme must selectively target and cleave the eggshell, and not other entities of enzyme molecules. Even enzymatic affinity for the fish larva itself should be avoided since this will damage the larva and expose it to serious risk of microbial and other diseases. Hence there is a straightforward biological rationale for why zonase should be non-selfdegrading.

Enzymatic activity similar to the zonase hatching enzyme of Atlantic salmon has been observed in eggs of several marine fish species. Since the proposal of Walther (1993; 2000) is that degrading of the zona by a zonase is a fundamental and general aspect of sexual reproduction, the implication is that zonase-like enzymes may be found in a wide variety of fishes and in other vertebrates, where they have so far gone undetected due to the need to follow special isolation procedures during purification.

The zonase according to the present invention is present in large amounts in the waste waters and hatching fluids of salmon eggs. In this crude aqueous state, salmon zonases may be effectively readied for purification by conventional techniques. This source of zonases offers a great advantage compared to isolation of enzymes from whole embryos, since it effectively obviates complications from extraneous biomaterial (eggshells, embryos and larvae). Thus, enzyme purification becomes greatly simplified.

An additional advantage is that the developmentally-staged salmon eggs may be transferred to minimal volumes of water prior to hatching. When highly synchronous hatching is induced by elevated (room) temperatures, or by deoxygenaton (Oppen-Berntsen et al. 1990), this yields a small volume of highly concentrated preparation of crude zonases.

A further essential aspect of the method is that, despite the increasing concentration of the proteolytic zonase, the stability of its resident zonase was observed to remain intact. Furthermore, it is important to note that this procedure yields zonase enzyme in a medium of almost pure water, containing at most 1 mM NaCl, but where zonases nevertheless possess and retain full enzymatic integrity over time. This preparation is therefore a valuable starting material for subsequent preparations of proteolytic zonases in various degree of purification, up to sequence-grade purity.

Zonase according to the present invention is a novel hatching enzyme of the serine-endoprotease family. This new enzyme has been shown to be non-selfdegrading. The inventors have purified the zonase to sequence grade, at which point it consist of only two closely similar enzymatic moieties. This was made possible due to the described method, which set forth the sequence in which the purification method has to be performed. The said zonase catalyses sequence specific endoproteolysis of peptide bonds C-terminal to basic amino acid residues, said specific endoproteolysis follows after the amino acids lysine or arginine. The zonase is further stable against inactivation conditions such as 4–8M urea or more, molar salt concentrations, distilled water and organic solvents such as at least 33% dioxane. It is resistant to auto inactivation both as dry substance and in aqueous solutions and retains its enzymatic activity in solution at about 15–30° C. preferably about 22° C. until 30–70 days preferably about 50 days, and in a solution at about 0° C. for more than six months. The zonase is inactivated in 10% (v/v) of β-mercaptoethanol and reactivated by removal of β-mercaptoethanol by evaporation by a temperature up to about 50° C.

The claimed zonase is a valuable tool for many well-known processes presently employing endoproteases. These include among many;

analytical work generating specific peptides from proteins (see Example 6), addition of endoproteases to laundry detergents to enhance the action of detergents and allow laundry washing at low temperatures, enhancing availability of costly ingredients for brewery processes, cleaning bakery utensils with little or no use of detergents to obtain bio-usable materials instead of waste, enhancing bioavailability of nutrients in feed by pretreating feed with proteases or using a neutral and stable zonase protease as a type of gastric digestive support in young fish and other newborn vertebrates.

The zonase from salmon is distinct from well known hatching enzymes from medaka ("chorionase"). By cloning and sequencing in salmon a gene homologous to the chorionase gene of the medaka, it was found that the enzyme resulting from transcription and translation of this gene did not crossreact at all with a highly specific polyclonal antibody to salmon zonase. Salmon zonase is thus a novel enzyme compared to known hatching enzymes.

EXAMPLE 1

Concentrated Preparation of Crude Zonase from Atlantic Salmon

The initial purification of zonases involves only filtration of hatched salmon eggs through cheesecloth. Such a filtrate may be frozen for years without significant zonase degradation, before being thawed and employed for further zonase purification. This fact greatly simplifies production of a starting material for purifying salmon zonases.

The next step involves adjusting the "zonase crude" to usually 4 M urea, which dissociates fragments of the salmon eggshell and allow their removal along with extraneous debris by low speed centrifugation (15,000 g; 2×15 min). This material shows no sign of clogging columns, which is a characteristic of crude materials prepared differently from what is described above. A "zonase crude" preparation suitable for purification by conventional chromatographic techniques is thus available. It is noteworthy that the salmon zonases are stable and catalytically active in 4, or even 8 M urea. Furthermore, this preparation of salmon zonase is effectively inhibited only by inhibitors of serine protease-type of proteases.

EXAMPLE 2

Purified Zonases from Atlantic Salmon

The product extracted from the "zonase crude" preparation may be chosen in different stages of purification. However, already after one round of gel filtration, the zonase is separated from the larger molecular components in the filtrate with a 12 fold purification with better than a 50% yield. Larger components present in the "zonase crude" seem for the most part to be soluble fragments of the eggshell, to which some zonase are bound tightly. It is essential that the high molecular weight contaminants are discarded at this early stage of purification, as their presence will otherwise interfere with, and block, the success of subsequent purification steps. In other words, the sequence in which the conventional purification methods are undertaken, is an essential aspect of the process. The matrix utilized may vary, but SEPHACRYL SR-200 is our usual choice. The buffer was Tris-HCl pH 8.0 or pH 8.5 (0.05 M) or Tris-Acetate (0.025 M, same pHs). The zonase obtained after gel filtration procedures account for the predominant zonase moieties in the "zonase crude", and the enzymatic activity was catalytically inhibited by benzamidine.

In terms of proteins, the zonase account for about 10% of the material already at this stage. This partly purified salmon zonase is again only inhibited by serine protease-type inhibitors.

EXAMPLE 3

Zonase as a Homogeneous Protein Product

Due to zonase inhibition by benzamidine, the enzyme fractions retarded on gel filtration columns, may be readily purified further by affinity chromatography on commercially available Benzamidine SEPHAROSE 6B-columns. This step allows 7.5 fold purification for an overall 94 fold total purification over the "zonase crude", with a yield of 37% of activity. The specific conditions utilized (with columns of 25 or 125 ml volumes) were again a 0.05 M Tris-HCl buffer (pH 8 or 8.5), which for removing non-specifically bound material on the columns, was adjusted to 1 M NaCl. Zonases are not removed by this step, as they remain tightly bound to the column. The success of this step is critically due to elution of zonases from the column using a 10–33% dioxane-gradient in 1 M NaCl in the same Tris-HCl buffer. This procedure hinges on the unusual stability of salmon zonases in organic solvents.

After affinty-purification, the zonase preparation exhibits one protein band on SDS-PAGE analysis, with a molecular weight of around 28 kDa. This moiety of zonase was strongly antigenic, allowing production of polyclonal antibodies, which specifically recognize salmon zonase, but not other salmon serine proteases such as salmon trypsins. Conversely, polyclonal antibodies to salmon trypsins do not recognize salmon zonase, establishing salmon zonase as a distinct product of embryonic salmon. However, this zonase product is not of sequence-grade purity, as revealed by Edman procedures for its N-terminal sequence. However, beyond the initial dozen N-terminal steps of sequencing, the overall amino acid sequence of this protein was shown to be similar to pure zonases. (The reason for the result is the presence of small inhibitory peptides during Edman sequencing procedures.) This highly purified salmon zonase preparation is also specifically inhibited only by serine protease-inhibitors.

EXAMPLE 4

Chemical Properties of Salmon Zonases

Gelfiltration-purified plus affinity-purified salmon zonases may be further purified to sequence-grade purity by one final chromatographic procedure. This procedure employs a PBE94 column, with a buffer of Tris-Acetate (10 MM, pH 9.0), where subsequent elution was with a salt gradient (up to 1 M NaCl salt) in this buffer. This step itself increases the catalytic activity of the zonase by a further 7.6 fold, (without removing significant amounts of proteins from the preparation), for an overall purification of 714 fold and with a yield of 28% from the starting material. This purification step leaves the protein identity of the zonases intact as a 28 kDa moiety. Hence, this step does not remove unrelated, major protein contaminants from the zonase preparation, as is customary for protein purification, but only small (inhibitory) peptides as also illustrated in Examples 2 and 3. The molecular weight of purified zonases is the same as observed by Western blotting technique for zonase moieties present in the hatching fluid and in the "zonase crude".

What apparently takes place in the third and final chromatographic procedure is the removal of oligopeptides with around a dozen residues, originating most likely from the eggshell and/or from the salmon embryo. These peptide contaminants appear to exert inhibitory effects on zonase catalysis, since their removal increases the catalytic activity of zonase. Also, their presence interferes with the first steps in the Edman sequencing of this zonase product. The two forms of zonases seen in this third purification step bind slightly differently to the column matrix. However, both forms have partial amino acid sequences which are identical or very similar.

Partial amino acid sequences from CNBr-generated peptides established the zonase as a distinct protein. Structural analysis yielded indications that the zonase may have distinct catalytic and substrate-binding domains, which may account for its sensitivity to calcium chelating agents when acting on macromolecular (physiological) substrates (binding is inhibited, hence catalysis is inhibited indirectly), and also sensitivity to serine protease inhibitors when acting on small substrates (catalysis is directly inhibited).

EXAMPLE 5

Chemical Properties of Salmon Zonases

The catalytic action of the zonase is unaffected by the, presence of salt in molar concentration, being nearly as effective in destined water as in 6M salt. The enzyme is essentially equally active between pH 7 and 9. However, zonase is inactivated below pH 4, and only weakly active at pH 6. Zonase is unaffected by the presence of 8 M urea. Zonase can be stored at room temperature (with and without urea) for fifty days with only minimal loss of enzymatic activity. Enzymatic activity is also not impeded by even 40% (v/v) of organic solvents such as dioxane or propanol. In contrast the enzyme is easily inactivated by 10% (v/v) of 2-mercaptoethanol, which may subsequently be removed by evaporation at 50° C. Catalysis is maximal at 42° C. (using the commercial substrate chromozym X (from Boehringer), with little, but significant catalytic action observed above 65° C., or after heating to up to 90° C. for 5 min, and subsequently cooled and assayed at room temperature.

EXAMPLE 6

Catalytic Characteristics of Salmon Zonases

The salmon zonases in question will cleave a whole series of chromozym substrates, with a maximal avidity displayed for peptide bonds with basic amino acids (preferably arginine). With these small artificial substrates, the zonases are as active as other serine proteases, but the $K_M$=14 $\mu$M, is lower. The Vmax is equal to 1.3 $\mu$M/min, and the Kcat is equal to 0.8 (1/sec). The high degree of specificity in terms of cleaving peptide bonds compared to other serine proteases such as trypsin, is shown by use of eggshell zr-proteins (Walther 1993) as substrate (Rong 1997): Trypsin will cleave these proteins into many small fragments, while zonase is observed to hardly degrade what is its physiological substrate, leaving large proteins as reaction products.

The observed specificity of salmon zonase action reflects of course exactly what is required of a zonase: Such enzyme must rapidly destroy the mechanical, but not the chemical integrity of the eggshell-proteins so that the embryo may exit from the egg, To do this in a rapid manner in the presence of extraordinary high amounts of the eggshell substrate, requires that only a minimal number of peptide-bonds are attacked specifically. This sequence-specificity in terms of proteolysis means that only about between 1 in 6, to 1 in 10 of the petidebonds that are potentially subjected to proteolysis are actually split in the case of the eggshell. For a variety of different proteins, the proportions of actual splits and potential targets may vary, also the exact proportion of actual splits and potentially targeted peptide bonds will vary with reaction conditions. Nevertheless, the zonases seem to possess excellent prospects in terms of accomplishing specific splits in various candidate proteins, as nowadays are achieved using commercial enzyme-preparations of enzymes possessing (other) site-specific properties, e.g. the Boehringer products Asp-N and Glu-C. Thus, zonases rank alongside commercial enzymes, which have found use in analytical work preparatory to protein sequenation, by yielding defined peptides from the large proteins to be sequenced. Thus, this trait of the enzymology of pure salmon zonases is commercially valuable.

We claim:

1. An isolated enzyme, denoted zonase, wherein said zonase occurs naturally in hatching fluid of salmon eggs, said enzyme being free of bound eggshell fragments, retaining serine protease activity specific to zona, being non-self degrading, and having an apparent molecular weight of about 28 kDa as determined by SDS-PAGE analysis.

2. The zonase according to claim 1, wherein said zonase is catalyzing sequence-specific endoproteolysis of peptide bonds C-terminal to basic amino acid residues.

3. The zonase according to claim 2, wherein said sequence-specific endoproteolysis follows after the amino acid lysine or arginine.

4. The zonase according to claim 3, which is resistant to auto-inactivation both as dry substance and in aqueous solutions.

5. The zonase according to claim 4, which is further stable against inactivating conditions, wherein said inactivating conditions are characterized by subjecting said enzyme to 4–8 M urea, molar salt concentrations, distilled water, organic solvents or a solution containing 33% dioxane.

6. The zonase according to claim 5, which retains enzymatic activity in solution at room temperature for 50 days, and in solution at 0° C. for more than 6 months.

7. Zonase according to claim 6, which is inactivated in 10% (v/v) of β-mercaptoethanol and reactivated by removal of β-mercaptoethanol by evaporation by a temperature up to 50° C.

* * * * *